(12) United States Patent
Dutari

(10) Patent No.: US 6,409,712 B1
(45) Date of Patent: Jun. 25, 2002

(54) MASCULINE HYGIENIC DEVICE FOR DAILY USE

(76) Inventor: Rodrigo Alberto Terán Dutari, P.O. Box 6-4024, El Dorado (PA)

(*) Notice: Subject to any disclaimer, the term of this patent is extended or adjusted under 35 U.S.C. 154(b) by 0 days.

(21) Appl. No.: 09/454,025

(22) Filed: Dec. 3, 1999

(51) Int. Cl.7 .................................................. A61F 13/15
(52) U.S. Cl. .................. 604/385.09; 604/346; 604/347; 604/349; 604/386; 604/387
(58) Field of Search ................................ 604/346, 347, 604/349, 386, 387, 385.09

(56) References Cited

U.S. PATENT DOCUMENTS

| | | | |
|---|---|---|---|
| 3,200,415 A | * 8/1965 | Breece, Jr. | |
| 3,463,154 A | 8/1969 | Hendricks | 128/287 |
| 4,059,114 A | 11/1977 | Richards | 128/287 |
| 4,197,849 A | * 4/1980 | Bostick | 128/295 |
| 4,551,142 A | * 11/1985 | Kopolow | 604/368 |
| D287,282 S | * 12/1986 | Ternstrom | D24/50 |
| 4,731,063 A | 3/1988 | Newkirk | 604/347 |
| 5,103,500 A | 4/1992 | Nager et al. | 604/359 |
| 5,290,270 A | 3/1994 | Fisher | 604/387 |
| 5,291,617 A | 3/1994 | Moretz et al. | 604/358 |
| 5,315,717 A | 5/1994 | Moretz et al. | 604/358 |
| 5,342,332 A | * 8/1994 | Wheeler | 604/349 |
| 5,392,467 A | 2/1995 | Moretz et al. | 604/393 |
| 5,414,870 A | 5/1995 | Moretz et al. | 604/378 |
| 5,435,014 A | 7/1995 | Moretz et al. | 604/393 |
| 5,486,168 A | * 1/1996 | Runeman et al. | 604/385.1 |
| 5,555,568 A | 9/1996 | Yon | 2/403 |
| 5,649,913 A | * 7/1997 | Cohen | 604/353 |
| 5,651,778 A | * 7/1997 | Melius et al. | 604/385.1 |
| 5,792,129 A | 8/1998 | Johansson et al. | 604/387 |
| 6,156,951 A | * 12/2000 | Gustafson et al. | 604/369 |
| D435,907 S | * 1/2001 | Mubiala | D24/125 |
| 6,197,011 B1 | * 3/2001 | Freitas et al. | 604/385.03 |
| 6,209,142 B1 | * 4/2001 | Mattson | 2/403 |

FOREIGN PATENT DOCUMENTS

| | | | | |
|---|---|---|---|---|
| GB | 2 099 706 | * 12/1982 | | A61F/5/44 |
| GB | 2 201 893 | * 9/1988 | | A61F/13/16 |
| WO | WO 87/07136 | * 12/1987 | | A61F/4/543 |
| WO | WO 89/00037 | * 12/1989 | | A61F/5/453 |
| WO | WO 89/11839 | * 12/1989 | | A61F/5/453 |
| WO | WO 91/07155 | * 5/1991 | | A61F/13/15 |

\* cited by examiner

*Primary Examiner*—John G. Weiss
*Assistant Examiner*—Bogart Michael
(74) *Attorney, Agent, or Firm*—Davis & Bujold, P.L.L.C.

(57) ABSTRACT

The present invention relates to a disposable garment shield device for men for use with an undergarment for the purpose of protecting the undergarment from staining and soiling due to secretions from the crotch region and genitalia of the user. The shield is constructed of a plurality of layered fabrics or materials designed to wick moisture and excretions away from the skin of the user and retain them in an absorbent layer of the shield. In addition to the soft, flexible and ergonomic nature of the device, a slit or cut is provided through a portion of the device to facilitate the extraction of the male genitalia for urination purposes in an ordinary manner in conjunction with a fly opening of a traditional male undergarment.

16 Claims, 5 Drawing Sheets

MASCULINE HYGIENIC DEVICE FOR DAILY USE

FIELD OF THE INVENTION

The present invention relates to a disposable hygienic sanitary device which is used in conjunction with a lower front part of a short, brief or other type undergarment, in particular for males and for the specific purpose of separating the male genitalia from direct contact with the undergarment while enabling a user increased accessibility for urination through an opening or accessibility slit in the device.

SUMMARY OF THE INVENTION

The hygienic device of the present invention is in general an anatomically conforming fluid reservoir and shield constructed as a substantially flexible composite formed from textiles, absorbent components and other suitable materials which are particularly comfortable and designed to be inserted as a shield between the user's body, specifically the crotch region, and the undergarment. The device is used to protect the user's body, the undergarment, and therefore inherently any outer garment as well, from contact with any bodily fluids, excretions or odors from the user's pelvic region. Specifically, the device separates the users genitalia from direct contact with the undergarment so as to avoid staining, soiling or discoloration thereof.

The composite is constructed from a specific layering of separate and differing materials in order to move moisture away from the skin of the wearer and to enhance the disbursement of the moisture of these fibers to a fabric in the composite which does not touch the skin, and to retain such moisture away from the users body as well as any undergarments or other clothing, thus protecting the user's skin, undergarments and clothing from any leakage or bodily secretions due to normal daily activities.

The present device is soft, comfortable and slim and is particularly effective for wicking moisture and or bodily secretions away from the skin of the wearer while not adding noticeable bulk to the crotch area of the undergarment. Typical moisture management garments include several layers of moisture absorbing material. Although such articles of moisture barrier material to prevent leakage through the garment onto outer clothing are known, often the presently available articles are expensive, bulky, and generally quite uncomfortable. Moreover, the known articles, devices and protective undergarments include a continuous, solid front panel constructed entirely of moisture absorbing fabric layers having no fly opening. As can be readily appreciated, the lack of a fly can create a problem for males, wherein the device becomes an obstacle rather than an aid, when it becomes necessary to urinate.

The present invention eliminates this problem by providing an absorbent protective and insulating undergarment protective article with a fly opening that does not compromise the undergarments ability to effectively absorb, retain and disburse moisture to drier areas of the undergarment for evaporation or retention. The particular fly opening or accessability slit of the present invention solves a long felt need for a device possessing the features of a normal undergarment with the addition of moisture management characteristics. Moreover, the crotch area of the user is better protected because the present invention is more anatomically conforming, softer, more absorbent and provides greater protection, while enabling normal everyday use for the user, and in particular the male user.

Additionally, this device is thin, soft, absorbent, impermeable, and very easy to put in and take out of the undergarment. Furthermore, the present invention is held relatively secure in a desired comfortable position while remaining fixedly attached in the desired position within the undergarment no matter what activity the user is involved in. The soft, flexible, comfortably thin hygienic device of the present invention does not need to be taken off or out of the undergarment to urinate, it is very discreet, it is not noticeable and may be easily stored and carried along with extra hygienic devices. These features enable the device to be taken off and on easily and disposed of quickly and needs few instructions for utilization.

The invention may also include, in or on one of the layers of the composite, chemical or medicinal elements, or deodorants incorporated therein in order to alleviate, or cure, any discomforts or conditions from which the user may suffer, and thus ensuring that the user, during daily activities, is more physiologically and psychologically secure. For instance, this embodiment prevents contact of perspiration soaked garments next to the skin over a period of time which can cause chafing, irritation and conditions conducive to bacteria, fungus and yeast growth which might not only become apparent to the user, but to others as well.

Therefore it is an object of the invention to provide a replaceable hygienic male garment shield device for use in combination with an undergarment, the hygienic device being placed in a user's crotch region between the legs and interposed between the user's body and the undergarment, the hygienic device comprising an elongate ergonomically contoured pad having at least a layer of flexible, moisture absorbent material having a front portion wider than a rear portion and a slit provided in the wider front portion of the pad and cut completely through the layer of material to create a closeable passage through the front portion of the device, the slit being in a substantially communicating correlation with a fly opening of the user's undergarment when the hygienic device is utilized in combination therewith.

It is another object of the invention to provide a masculine hygienic device which includes a composite layering of material having moisture absorbent characteristics.

It is another object of the invention to provide a masculine hygienic device which provides the function of an ordinary undergarment for males while also having improved moisture management and retention characteristics.

It another object of the invention to provide a moisture management device for use with everyday garments designed for general wear without noticeable bulk.

It is another object of the invention to provide a masculine hygienic device which includes an attachment for securely and comfortably affixing the device within an undergarment of the user.

It is a further object of the invention to provide a hygienic device which protects the undergarments as well as the outer clothing of the user from stains, discoloration, soiling and impregnations thereby lessening the need for constant washing of the clothing.

A still further object of the invention is to provide an accessability slit, either horizontal or vertical, in the device which allows for access to the male genitalia for urination purposes in a normal manner with common place contemporary male undergarments.

Another object of the invention is to provide a layer of the material wherein a chemical or medicinal or deodorant element is incorporated in order to alleviate, cure, or protect the user during normal daily activities.

Another object of the invention is to provide a device which can be individually wrapped and yet discreetly carried without drawing attention thereto.

It is also an object of the invention to provide a number of sizes, in particular small, medium and large in combination with the hygienic device in order to accommodate a large range of users.

Therefore, it is an even further object of the invention to provide a system of adhesion or adhesive bands attached to the outermost layer of the hygienic device to secure the device within the lower front portion of the undergarment.

It is another object of the invention to provide a moisture management composite device constructed from integral multilayered materials which can be easily fabricated without extensive labor.

DETAILED DESCRIPTION OF THE PREFERRED EMBODIMENTS

Figure 1:
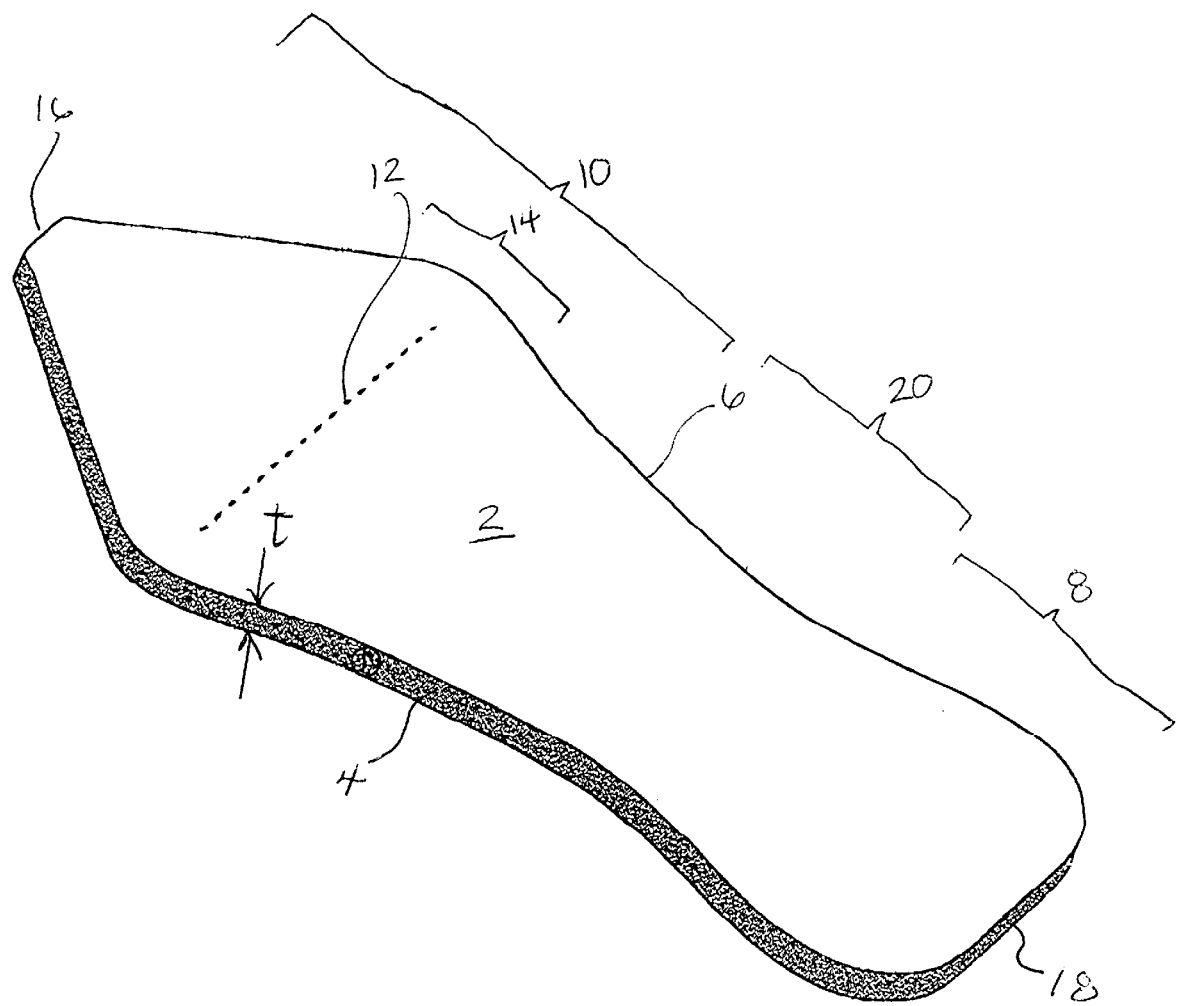
FIG. 1 is a top perspective view of the male hygienic device showing the general thickness, shape and detailing the general alignment and arrangement of the male accessability slit.

Referring now to FIG. 1 of the drawings, the hygienic device 2 of the present invention will now be described. The device 2 is formed in general having an anatomically form fitting shape in order that proper positioning and wearing of the device 2 between the skin and genitalia of the user and an undergarment (not shown), particularly a male brief or boxer style undergarment, is as natural and comfortable as possible. The device 2 is substantially elongate and flexible having a first side 4 and a second side 6 separated by a front edge 16 and a rear edge 18 and having a thickness t which is a relatively constant thickness throughout the device 2.

The first and second sides 4, 6 and front and rear edges 16, 18 define the ergonomically shaped device having several distinct portions or regions. The front edge 16 and adjacent first and second sides 4, 6 define a wider forward most portion 10, the first and second sides 4, 6 than converge from the wider forward most portion 10 to a substantially central narrow waist portion 20 before widening again slightly to form a rearward portion 8. A further detailed discussion of the portions follows below.

Figure 2:
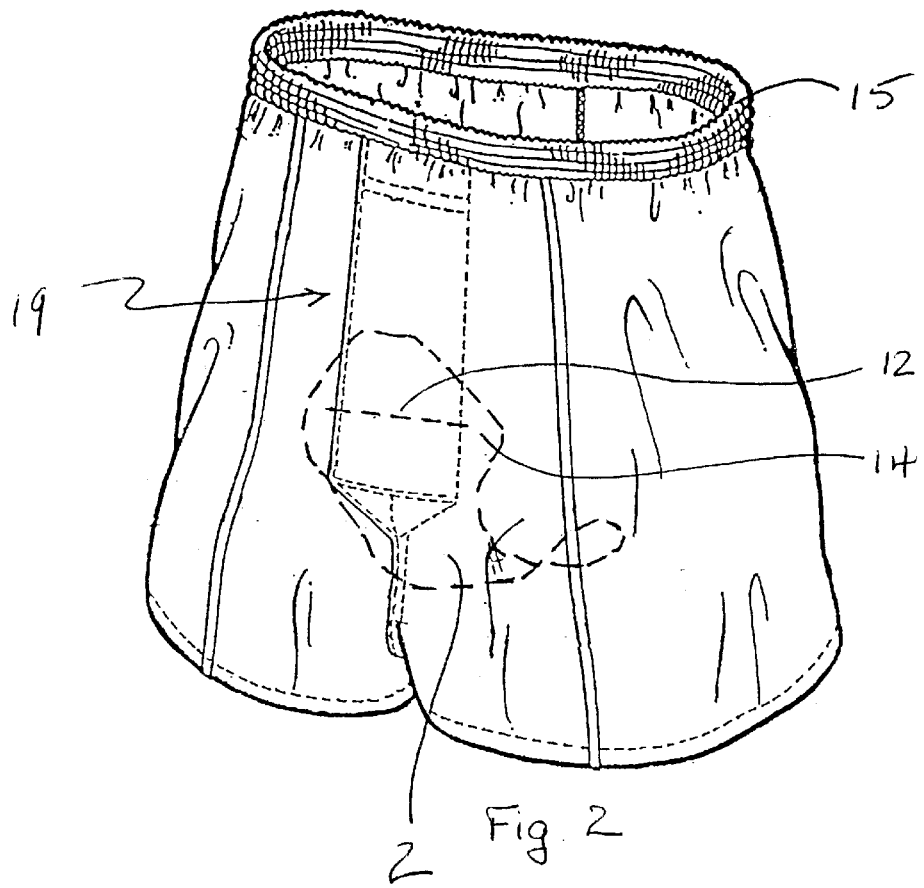
FIG. 2 is a perspective view of a traditional boxer style undergarment having a device inserted in conjunction with the fly 19.
Figure 3:
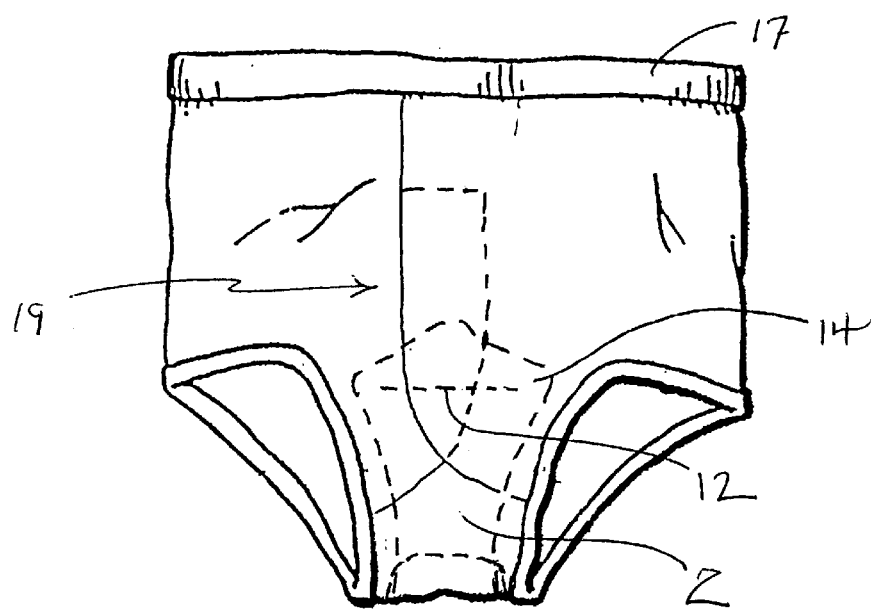
FIG. 3 is a front view of a traditional brief style undergarment having a device inserted in conjunction with the fly 19.

As is apparent from FIGS. 2 and 3, the waist 20 and rearward portion 8 are intended to be located in the lower forward crotch area of a traditional male undergarment, specifically a boxer 15 or brief 17 style undergarment, and designed to fit comfortably between a user's legs without causing discomfort or chafing between the inner thighs of the user while ensuring that there is no rearward leakage of fluids. The wider forward portion 10 protrudes forward from between the innerthighs of the user and follows the general contours of the user's body upwards in conjunction with the crotch portion of the undergarment 15, 17. The wider forward portion 10 further includes a widest most portion 14 to securely and comfortably cradle or encompass the user's genitals and which is located substantially adjacent the fly 19 of the undergarments 15, 17.

The device 2, as shown in FIGS. 1, 2 and 3 reveals only a single material for simplicity's sake, however, the device 2 is generally a multi-layered composite of different fabrics or materials wherein each of the layers performs a different function to further the absorbability and protection of the user. A further discussion of such layering is provided below.

Distinctive to the present invention is the access slit 12 found in the wider forward portion 10 of the device 2. The access slit or cut 12 passes through the entire thickness t of the device 2 and extends substantially perpendicularly between the first and second sides 4, 6 at least partially across the width of the forward most portion 10 of the device 2. In general, the slit or cut 12 is located across the widest portion 14 of the device 2. Although as would be apparent to anyone of ordinary skill in the art, the slit 12 could be positioned and oriented in any number of different ways, a further discussion of possible orientations and locations will follow.

The widest portion 14 of the device 2, which is generally located in contact with and encompassing or cradling the genitals of the user, is provided with the slit or cut 12 there through which extends from near the first side 4 of the widest most portion 14 of the device across and through the entire thickness t of the device to near the second side 6 of the widest most portion 14 of the device 2. As can be readily ascertained by one of ordinary skill in the art, with the slit 12 located adjacent the genitals of a male user, the user can facilitate the extraction of the male genitalia for urination purposes without the need for removal of the device or undergarment. Such a slit 12 which is located adjacent the male genitals also enables the male user to utilize the fly 19 of typical brief or boxer style 15, 17 everyday underwear as effectively as if the device 2 were not being worn at all.

The particular dimensions of the hygienic device 2 of the present invention will now be described in detail with reference to FIG. 1. The first and second sides 4, 6 are separated by a front and rear edge 16 and 18, respectively. The forward most portion 10 of the device 2 ranges in size from the front edge 16 wherein the first and second sides 4,6 are separated by several millimeters, to the widest most portion of the device 14 which can separate the first and second sides 4,6 by many centimeters. This widest most portion 14 is, as discussed above, intended to cradle or encompass the genitalia and also includes the slit or cut 12 through the device extending between the first and second sides 4, 6 substantially the same distance as the width of the widest most portion 14.

From the forward most portion 10 and widest portion 14 of the device, the first and second sides 4, 6 contour inwardly towards one another to create the central waist portion 20 which can be of substantially lesser dimension than the widest most portion 14. The waist portion 20 may be from several millimeters to many millimeters in width depending upon the particular bodily dimensions of the user. The sides 4,6 defining the waist 20 then contour outwardly expanding into the slightly wider rearward portion 8, the first and second sides 4,6 generally tending outwards from one another to form the rearward most portion 8 which is usually of slightly greater width than the waist portion 20. The rearward most portion 8 is intended to extend slightly behind the thighs of the user such that no rearward leakage of fluid is allowed between the user's buttocks.

The relative thickness of the device 2, which is approximately 4 mm, adds very little to the bulk or weight of the undergarment and therefore also facilitates the extraction of the male genitalia through the slit or cut 12 and the fly of the undergarment for urination purposes. As the extraction and use of the male genitalia for purposes of urination is well know to those of ordinary skill of the art no further description is provided herein.

Figure 4:
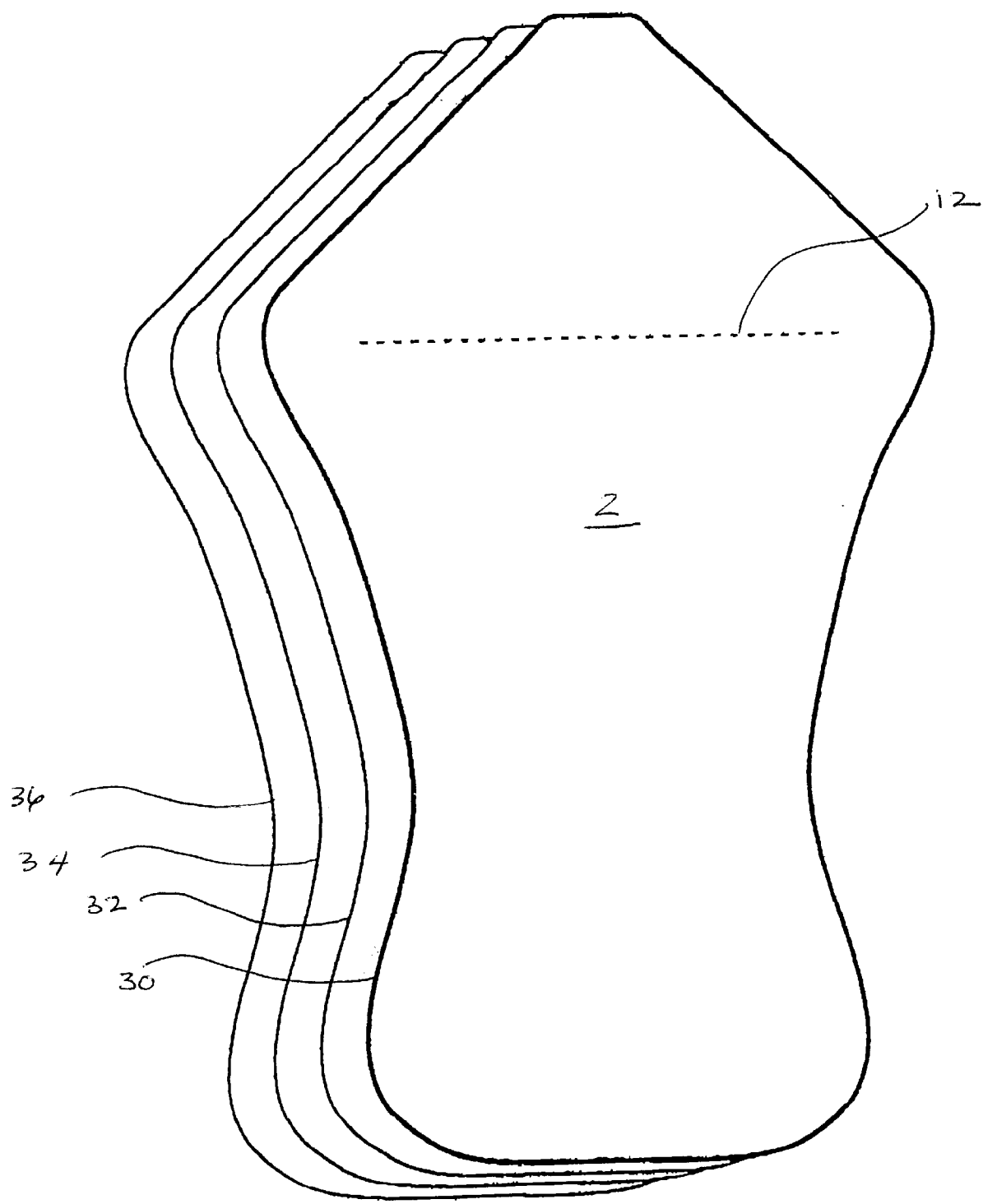
FIG. 4 shows a top perspective view indicating the differing types of layers in the composite as well as the number of layers contained in the device.

Turning now to FIG. 4, the composite layering of materials of the device will be described. In general the layering will be described from a primary layer 30 in contact with the users body outwards towards the undergarment.

The primary layer 30 being located next to and in contact with the user's skin is an insulating layer which can be any type of soft comfortable fabric known in the art which is generally a moisture permeable hydrophobic fabric which facilitates wicking and evaporation of fluids from the skin of the user. This insulating layer 30 is positioned next to the skin of the wearer for reasons of comfort and its ability to wick moisture away from the skin of the user. Typical fabrics or materials which can be used for the insulating layer can be made from a fiber group comprising polyester, polypropylene, and nylon fibers, although blends of other fibers, including cotton and rayon may be utilized as well.

Secondly, a protective layer 32 is designed to separate the insulating layer 30 from an absorbent layer 34 to be discussed in greater detail below. The protective layer 30 is generally also hydrophobic and may be constructed of any such material with these known characteristics. The protective layer is generally designed to allow moisture to pass one way, away from the body of the user and the insulating layer 30 and into the absorbent layer. The protective layer may be made from fabric chosen from the group comprising polyester, cotton, rayon, nylon, polypropylene, and a blend of polyester and cotton.

Thirdly, an absorbent layer 34 may be made of any type of moisture retaining fabric or material as is known in the art. The absorbent layer 34 will retain the majority of the moisture, liquid or secretions passed through the hydrophobic insulating and protective layers away from the body of the user. Materials that are available for use and contemplated, although others can be used include; cloth, cotton, paper, cellulose, natural fibers and synthetic fibers. It is contemplated that to retain the required minimal thickness t of the present invention that superabsorbant fabrics may also be used which, when absorbing fluid, bind the absorbed fluid chemically.

Lastly, the fourth layer 36, and the outermost layer from the user's body and which is generally adjacent and in contact with the undergarment is an impermeable layer 36 which is designed to keep all absorbed moisture, liquid and secretions, etc. from passing through the hygienic device 2 and staining or coming in contact with the undergarment of the user. This impermeable layer can be any number of materials or fabrics currently available. The impermeable layer may comprise a plastic sheet, hydrophobic non-woven material or may be part of a plastic and non-woven laminate structure all of which are preferably air permeable.

These four layers may be joined in any manner as is known in the art such as glueing or ultrasonic and heat welding, to work in conjunction to provide a soft, light weight, thin absorbent and impermeable hygienic device which is easy to utilize, dispose of and is flexible, comfortable and functional. It is also to be appreciated that a cream ointment or medicine could also be applied or spread on the insulating layer such that it is in contact with the skin. For instance, an anti-fungal powder or cream which could be manufactured into the insulating layer and therefore would be disseminated to and absorbed into the skin of the user during the use of the present hygienic device.

Figure 5:
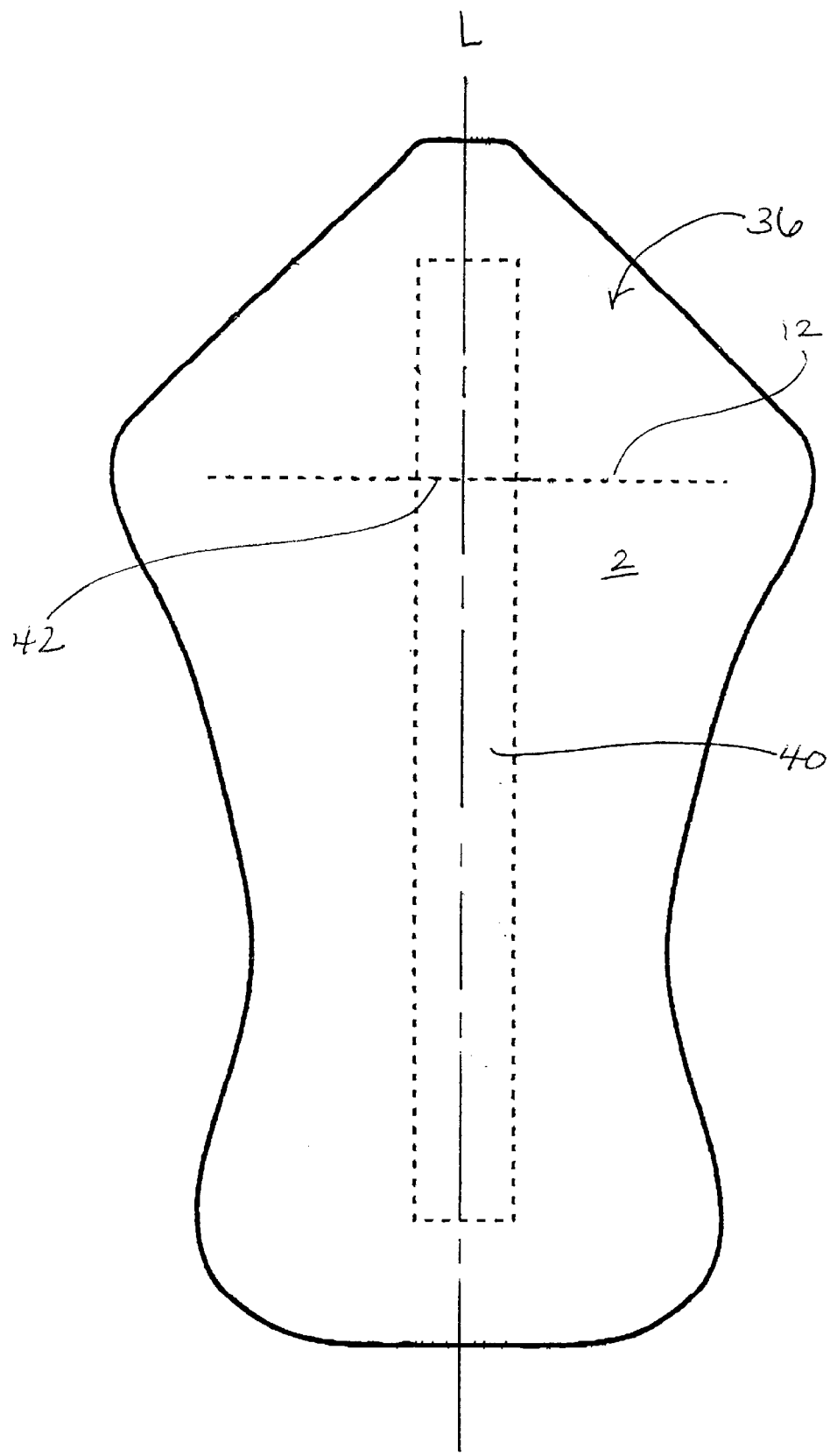
FIG. 5 is a bottom view of the hygienic device showing the male accessability slit as well as an adhesive strip aligned generally down the middle of the device.

Referring now to FIG. 5, a bottom view detailing the adhesive band 40 necessary for applying and affixing the hygienic device 2 within the undergarment of the user is shown. An adhesive band 40 is generally fixed along a longitudinal axis L of the hygienic device 2 and is intended to securely affix the device 2 to an inner surface of the undergarment. The adhesive band 40 may utilize any commonly used adhesive on the market and may be of any necessary width and tackiness necessary to properly affix the device. In general, it is a flexible elongate adhesive band extending substantially the length of the device 2 and having a width not exceeding that of the dimensions of the second and first sides of the device. Atypical strip of adhesive several inches long and approximately an inch wide and located proximate the long axis L of the device along the impermeable layer 36 would suffice.

While only one adhesive band 40 is shown it would be apparent to those skilled in the art that several adhesive bands would facilitate even a more secure placement. Further, the adhesive band 40 is also discontinuous or cut at the point 42 where it overlaps with the substantially horizontal slit or cut 12 through the hygienic device 2. As is readily apparent such a cut is imperative so that it does not impede use of the accessibility slit.

The adhesive 40 is placed on the impermeable layer 36 and while in the packaging is provided with a removable disposable cover or release liner (not shown) such that for use, the liner or cover is removed and the impermeable layer 36 and adhesive band 40 placed in a comfortable position in the undergarment and such that the adhesive band 40 adheres to the undergarment in the proper comfortable position.

Figure 6A:
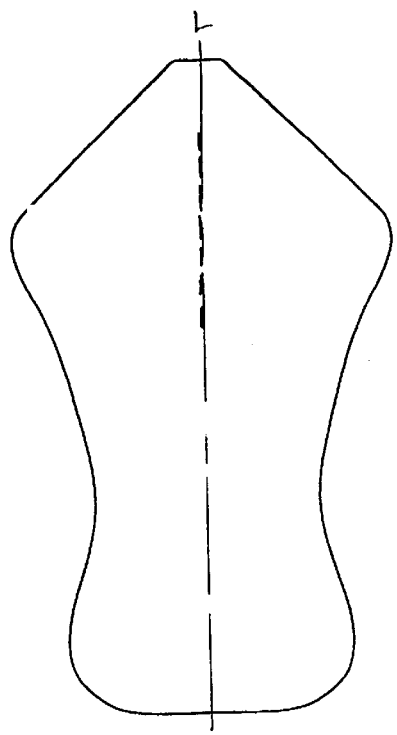
FIGS. 6a–6d are top views showing optional orientation and shapes of the male accessability slit in the hygienic device.
Figure 6B:
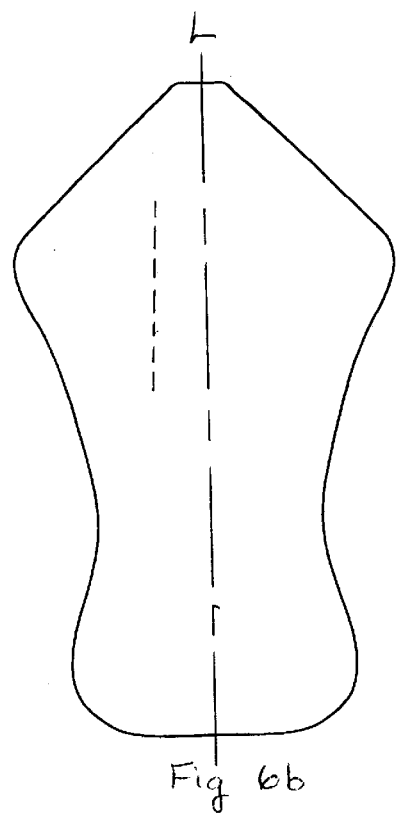
Figure 6C:
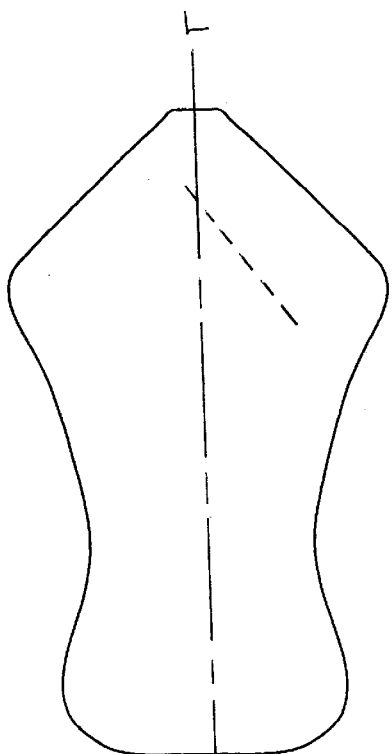
Figure 6D:
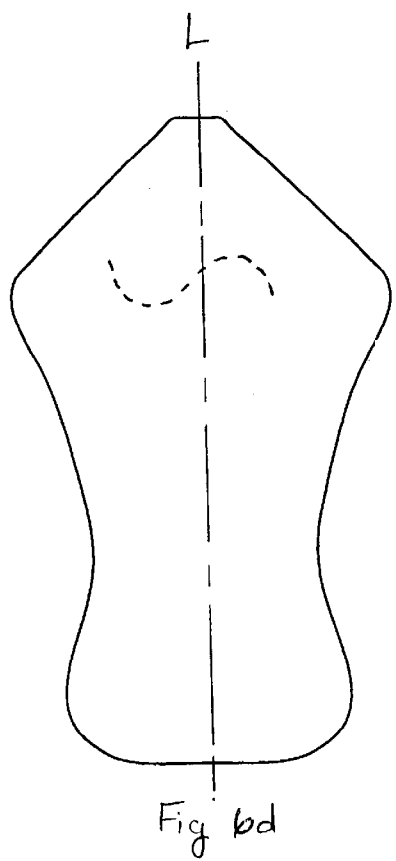

FIGS. 6a–6d detail alternative embodiments of the present invention wherein the slit or cut 12 is provided substantially along or in parallel with the longitudinal axis L, as well as at an angle with respect to the axis L. This positioning of the slit or cut 12 matches in particular with the numerous male brief style undergarment and may in particular match the placement and style of various fly positions in traditional male undergarments. It should be noted that placement of the slit or cut 12 in many different positions relative to the longitudinal axis L, whether perpendicular, parallel or at an angle such as shown in FIGS. 6a–6d would be apparent to those skilled in the art and thus should be considered only a sample of the positioning which could be utilized. Furthermore, as shown in FIG. 6d, it should also be observed that the slit 12 does not have to be linear, any number of curves or linear deviations could be incorporated into the slit 12 to facilitate proper positioning and ease of use.

The device 2 may be marketed in an individual manner or in boxes containing a number of individually wrapped devices 2. The individually wrapped devices (not shown) are intended to be discretely and easily carried in a pocket, brief case, sports bag, glove compartment and quickly and easily replaced and disposed of. While the device 2 would be generally available in sizes ranging from small, medium and large, it will be apparent that a device of this nature could be produced in almost any size necessary as well as incorporating fragrances, deodorants and medicines.

Since certain changes may be made in the above described invention without departing from the spirit and scope of the invention herein involved, it is intended that all of the subject matter of the above description or shown in the accompanying drawings shall be interpreted merely as examples illustrating the inventive concept herein and shall not be construed as limiting the invention.

I claim:

1. A replaceable male hygienic device being placed in a user's crotch region between the legs and interposed between the user's body and an undergarment, the hygienic device comprising:

a single panel defining an elongate ergonomically contoured moisture absorbent pad comprising at least a first layer of flexible, moisture absorbent material defining a forward portion wider than a rear portion; and a single slit provided in the wider front portion of the pad and cut completely through the single panel to create a passage through the forward portion of the device.

2. The hygienic device as set forth in claim 1 wherein the single panel pad is formed from a plurality of contiguous layered materials including at least an insulating layer, a protective layer, an absorbent layer and an Impermeable layer.

3. The hygienic device as set forth in claim 2 wherein the Insulating layer is a soft hydrophobic material.

4. The hygienic device as set forth in claim 3 wherein the protective layer is a hydrophobic material.

5. The hygienic device as set forth in claim 4 wherein the absorbent layer is a hydrophillic material.

6. The hygienic device garment shield as set forth in claim 5 wherein the plurality of layered materials are contiguously combined to produce a pad thickness of approximately 4 mm in thickness.

7. The hygienic device as set forth in claim 2 wherein an adhesive is affixed to an outwardly facing side of the impermeable layer to removably secure the pad in contact with the undergarment of the user.

8. The hygienic device as set forth in claim 2 wherein the accessibility slit is positioned and aligned on the front portion of the device to allow direct communication with a fly opening of the undergarment.

9. The hygienic device as set forth in claim 8, wherein the slit is cut in the front portion substantially along a longitudinal axis of the shield.

10. The hygienic device as set forth in claim 9, wherein the slit cut in the front portion is substantially linear.

11. The hygienic device as set forth in claim 9, wherein the slit cut in the front portion is substantially non-linear.

12. The hygienic device as set forth in claim 9, wherein the slit is cut offset from and parallel with the longitudinal axis.

13. The hygienic device as set forth in claim 9, wherein the slit is cut at an angle with respect to the longitudinal axis.

14. The hygienic device as set forth in claim 9, wherein the slit is cut perpendicular to the longitudinal axis.

15. A replaceable male hygienic device being placed in a user's crotch region between the legs and Interposed between the user's body and an undergarment, the hygienic device comprising:

a single panel defining an elongate ergonomically contoured moisture absorbent pad comprising at least a first layer of flexible, moisture absorbent material defining a forward portion wider than a rear portion;

a single slit provided in the wider front portion of the pad and cut completely through the single panel to create a passage through the forward portion of the device; and wherein the single panel pad is formed from a plurality of contiguous layered materials including at least an insulating layer, a protective layer, an absorbent layer and an impermeable layer and the insulating layer is a soft hydrophobic material.

16. A disposable male hygienic device for inseparable combination with an undergarment having a fly opening, the device being positioned adjacent the user's skin between the skin and undergarment in a crotch region of the undergarment, the device comprising:

an thin elongate ergonomically contoured panel formed from at least a layer of moisture absorbent material having a first and second edge separated by a front edge defining a wider forward portion narrowing to a waist and a rearward portion defined by the first and second sides separated by a rear edge;

the front portion including a substantially pointed front end widening to a widest most portion of the panel to provide an increased area of protection and moisture absorption in an upper crotch region;

the waist and rearward portion being substantially narrower than the front portion to fit between a user's legs and provide protection and moisture absorption in a lower crotch region;

a slit, cut substantially perpendicular to the first and second edges and substantially across the widest most portion of the front segment; the slit passing completely through the contoured panel to form a passage there through for communication between the slit and the fly of a user's undergarment;

wherein the pad is formed from a plurality of layered materials including at least an insulating layer, a protective layer, an absorbent layer and an impermeable layer, the slit is cut in the front portion substantially along a longitudinal axis of the shield offset from and parallel with the longitudinal axis.

* * * * *